United States Patent [19]

Williamson

[11] Patent Number: 5,413,590
[45] Date of Patent: May 9, 1995

[54] SKIN TREATMENT DEVICE

[75] Inventor: Neville L. Williamson, Wellington, United Kingdom

[73] Assignee: Innovative Medical Devices (UK) Ltd., United Kingdom

[21] Appl. No.: 182,059

[22] PCT Filed: Jul. 13, 1992

[86] PCT No.: PCT/GB92/01273
§ 371 Date: May 2, 1994
§ 102(e) Date: May 2, 1994

[87] PCT Pub. No.: WO93/01860
PCT Pub. Date: Feb. 4, 1993

[30] Foreign Application Priority Data

Jul. 17, 1991 [GB] United Kingdom ............... 9115391

[51] Int. Cl.6 ................................. A61N 1/04
[52] U.S. Cl. ........................................ 607/75
[58] Field of Search ............... 607/75, 76, 150, 151

[56] References Cited

U.S. PATENT DOCUMENTS 5,314,423 5/1994 Seney ................................. 607/46

FOREIGN PATENT DOCUMENTS 2128093 10/1982 United Kingdom .
2181056 3/1990 United Kingdom .

Primary Examiner—William E. Kamm
Assistant Examiner—Scott M. Getzow
Attorney, Agent, or Firm—Learman & McCulloch

[57] ABSTRACT

Skin treatment device (FIG. 1) comprises a housing (10), conveniently a plastics moulding, contains a low-tension D.C. power circuit including a battery (21), the negative pole being connected through a flexible lead (20) to a probe (16) having a metal electrode tip (22) for application to a localized area of the users skin requiring treatment. The tip is conical terminating at an acute point and having an included angle of taper of preferably around 50 deg. for non-invasive application to the skin. The positive pole is connected to a second electrode (26) constituted by a portion of the housing which will be gripped in the user's hand completing the operative circuit through the user's body.

13 Claims, 2 Drawing Sheets

SKIN TREATMENT DEVICE

This invention relates to devices for non-invasive treatment of localised skin disorders, for example comedones such as black heads, and pustules, by applying an electric current thereto.

GB-A-2181056, GB-A-2035805, GB-A-1471565, GB-A-1416141 and GB-A-706219 are examples of prior proposals for such treatment devices. In some of these, electrodes in the form of fine needles or wires have to be actually inserted within the affected tissue but such invasive treatment carries risk of infection and may only be suitable for use by medically qualified or other skilled operators.

The object of the present invention is to provide a treatment device which is particularly safe, effective and convenient in use; which can readily be used by a subject for self-treatment as and when required; and which can be provided in a compact and inexpensive form.

According to the invention there is provided a skin treatment device comprising a housing containing a low-tension battery-energised D.C. power source; an insulated probe carrying a first electrode operatively connected to the negative pole of said source by a flexible lead and having an electrically conductive tip to be applied non-invasively to a point on the subject's skin requiring treatment; and a second electrode operatively connected to the positive pole of said source to be gripped or otherwise contacted by the subject in use characterised in that said tip of the first electrode is conical in shape terminating at an acute point having an included angle of taper within the range of from 45 to 60 degs., and preferably around 50 degs.

The proximal part of the latter electrode preferably has a diameter of not more than 4 to 5 mm at its merging with the greatest diameter end of the tapered tip.

It is also preferred that at least said tip of the first electrode is formed from a hard corrosion-resistant metal, for example stainless steel to resist distortion or damage to said acute point and to facilitate the effective cleaning and sterilization of the tip e.g. by use of an antiseptic.

The current operatively applied through said tip is preferably less than 2 ma and may be around 0.7 to 0.9 ma.

To ensure that only the acute point of the first electrode can contact the skin so that the applied current is concentrated thereat said tip may be sheathed in an insulating material, leaving only said point exposed.

The second (positive) electrode may be constituted by a portion of said housing, the latter being shaped to be gripped in the subject's hand for electrical contact therewith. An appropriate portion of the housing may be rendered electrically conductive by being moulded or otherwise formed from a plastics compound which includes a metal powder.

Preferably the device will include an indicator light or other indicator device to show when current is flowing through the electrode circuit.

The housing may include or carry a mirror, advantageously a magnifying mirror, to facilitate the accurate application of the first electrode point to the desired location on the skin, particularly on the subject's face and/or it may incorporate an illuminating light source which may be powered electrically from the same or another battery carried in the housing, to facilitate viewing of the affected area of the skin.

The D.C. power source may include a 9 volt battery and a resistor in series with the electrodes, e.g. a 15 to 10 Kohm resistor, to drop the current at the electrodes to said level.

An embodiment of the invention is now more particularly described, by way of example, with reference to the accompanying drawings wherein.

The device includes a housing 10, conveniently of moulded plastics, a lower part of which is shaped to be conveniently gripped in a user's hand and the upper part being of circular shape viewed in elevation.

Figure 2:
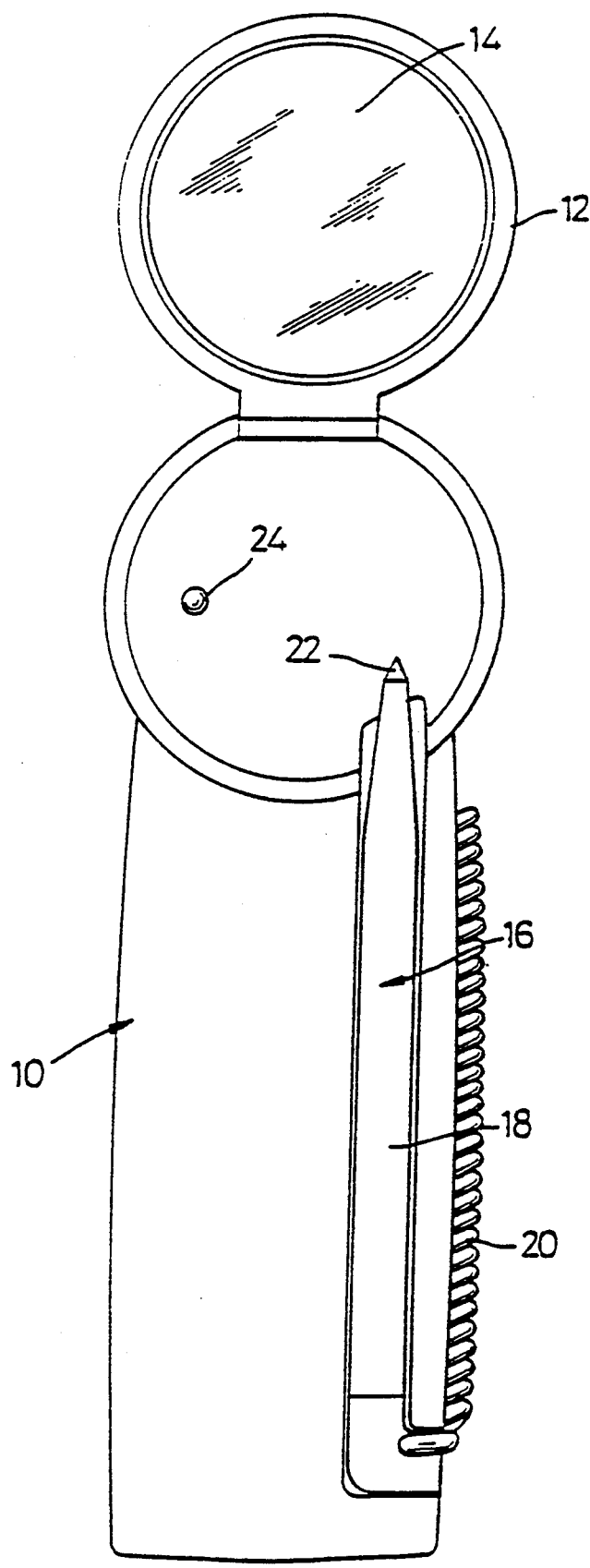
FIG. 2 is a front elevation of the device.
Figure 3:
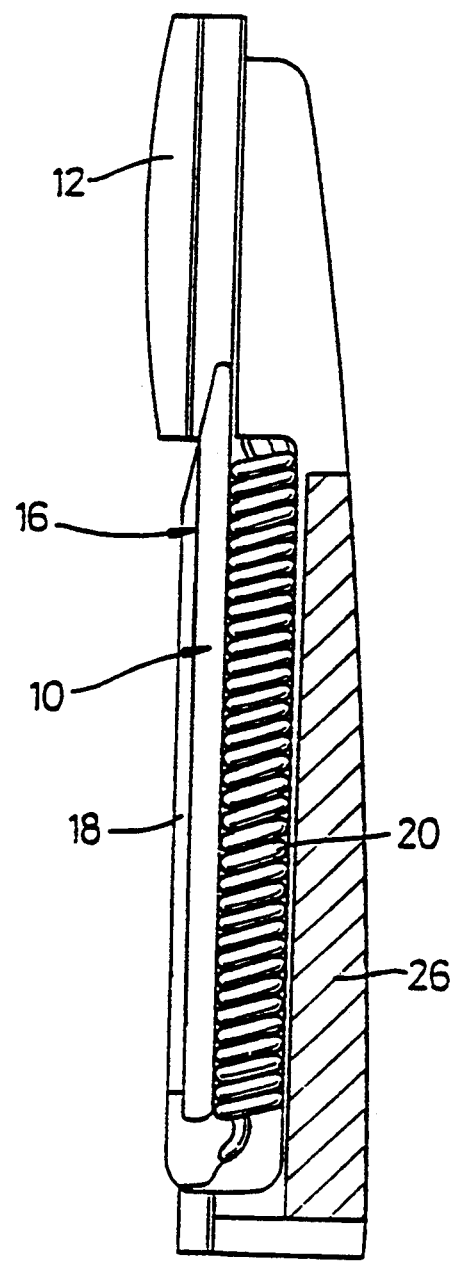
FIG. 3 is a side view thereof.

A circular hinged flap 12 (FIGS. 2 and 3) overlies the front of said upper part in the manner of a lid in its closed condition (FIG. 3) and mounts a concave magnifying mirror 14 on its inner face which can be viewed when the flap is swung up to an open condition (FIG. 2).

A probe 16 having an insulated sheath 18 to be held in the fingers is connected to housing 10 by an insulated flexible lead 20. When the probe is not in use it is stowed by being clipped into a longitudinal slot in the front of housing 10 with its tip extending onto the upper part of that housing so that it will be covered and protected by flap 12 when the latter is closed. The flexible lead 20 is of the resiliently coiled type so that it will retract automatically to lie neatly along the side of housing 10 when the probe is stowed.

The lower part of housing 10 contains a 9 volt dry battery 21 having its negative pole connected through lead 20 and its continuation through sheath 18 to a pointed metal tip 22 of the probe 16, constituting a negative electrode, which will be further described hereafter.

A resistor is connected in series between the negative pole and probe 16 and said connection also passes in series through a low current indicator light 24, e.g. an L.E.D. which is mounted in the front wall of said upper parts of housing 10 so that it is visible to the user when flap 12 is open but is protected by the latter when shut.

The positive pole of battery 21 is connected to the exterior face of the lower part of housing 10 at least an area of which, e.g. the back and sides, is formed of or coated with metal, metalised material e.g. a plastics mix including metal powder, or some other electrically conductive material so that the positive side of the battery makes contact with the user's hand when gripping the housing. Such a metal coated or metalised area is indicated at 26 on the drawings and constitutes a positive electrode.

Preferably resistor 23 has a value of 15 to 10 Kohm so that the current applied at the probe tip 22 is less than 2 ma and preferably around 0.7 to 0.9 ma.

Figure 1:
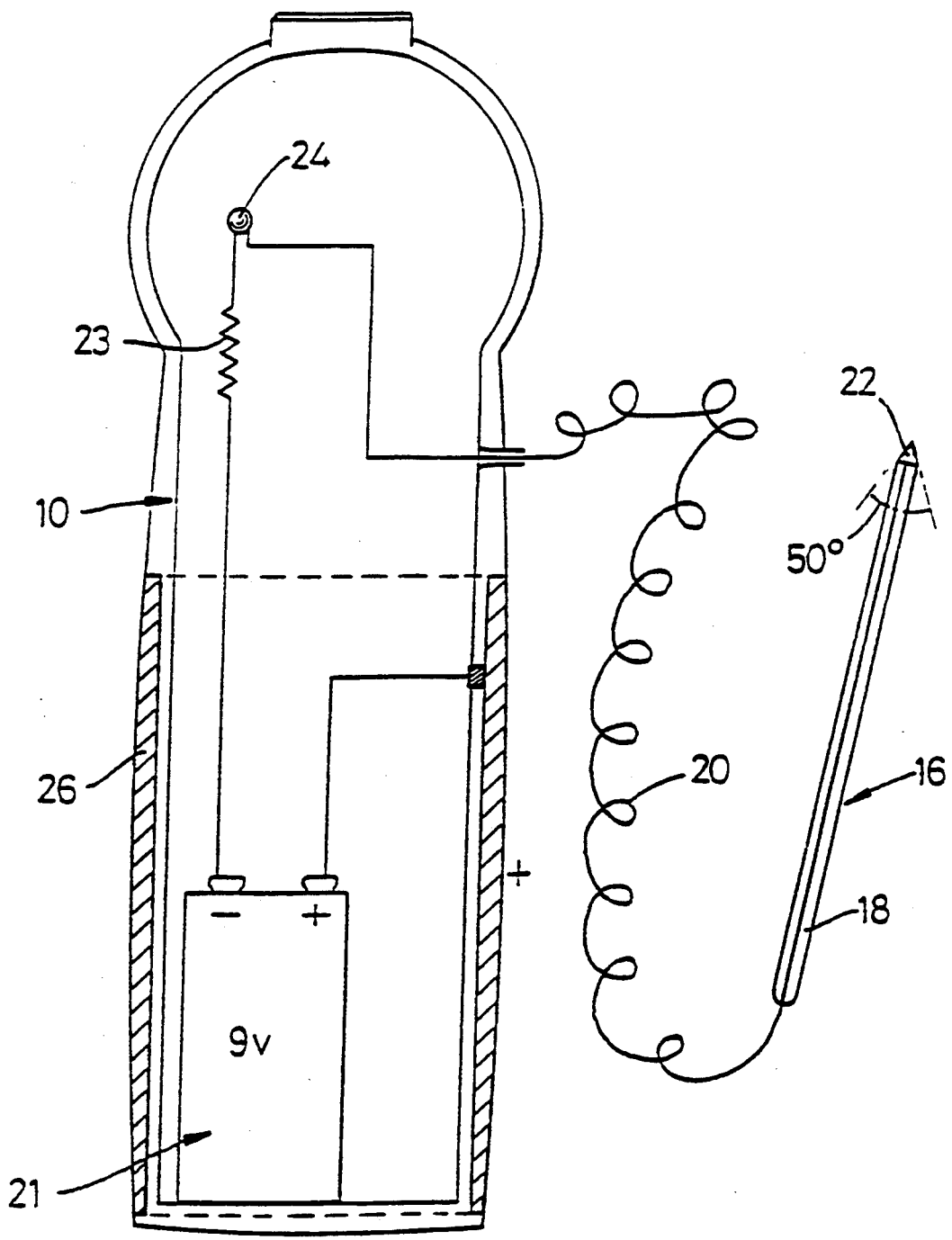
FIG. 1 is a sectional diagram of an electrical treatment device illustrating its circuitry.

Tip 22 of probe 16 has a true conical shape i.e. it terminates at an acute point not a rounded end, the angle of the cone in diametral section being between 45 and 60 degs and preferably around 50 degs as indicated on FIG. 1.

It has been found that a tip of this shape provides accurately positioned and reliable and effective point electrical contact with the skin for safe and localised electrical treatment thereof non-invasively i.e. without actual penetration, and without leaving any residual bruising as is the case with some electrical treatment probes having larger or rounded tips.

Moreover a pointed tip which has too great a cone angle obstructs viewing of the point on the skin to be treated while a very acute angle would form a sharp point with risk of scratching or pricking the skin. The greatest diameter proximal end of the tip is not more than 4 to 5 mm in diameter, again to ensure easy viewing of the point of contact.

So that only the very point of the tip 22 can make electrical contact, the side face of the conical tip is preferably coated in an insulating material leaving only the extreme point exposed. This ensures correct point application of the electric current even if the probe is held at an angle so that the side of the cone contacts the skin surface.

The current level is such that there is no risk of burning the skin but it is found that application of the probe tip to an affected area e.g. a comedon or other infected pore of the skin or to analogous skin infections or disorders such as pustules is extremely efficacious in countering the localised infection and promoting speedy healing. Use of the device is extremely simple, the user grips housing 10 in one hand while holding the insulated sheath 18 of the probe 16 in the fingers of the other hand, centering tip 22 on the affected point or area e.g. on the face, with the aid of the mirror 14. The electrode circuit is completed automatically when the tip 22 is applied to the skin through the user's body and back through the hand contacting the electrically conductive area 26 of the housing to connect to the positive pole of the battery. When the circuit is completed in this way the indicating light 24 will be illuminated, thus the user is aware of when current is flowing. The application is usually effective if continued for around 5 to 20 seconds. The power consumption is low for complete safety and long battery life.

The metal probe tip 22 is preferably formed from a hard and inert corrosion-resistant metal e.g. stainless steel and it can readily be cleaned and sterilised after use with a suitable antiseptic.

With the probes stowed as described above the tip 22 is fully protected and electrically isolated and the device is compact so that it can readily be carried in the pocket, handbag or toilet bag.

With the above arrangement an ON/OFF switch is not essential though one may be included in the circuit if desired. A battery powered lamp for illumination of the area being treated may also be included, e.g. mounted on the housing on or adjacent to mirror 14 and powered from battery 21 or from a separate battery carried in the housing.

I claim:

1. A skin treatment device comprising a housing (10) containing a low-tension battery-energised D.C. power source (21); an insulated probe (16) carrying a first electrode operatively connected to the negative pole of said source by a flexible lead (20) and having an electrically conductive tip (22) to be applied non-invasively to a point on the subject's skin requiring treatment; and a second electrode (26) operatively connected to the positive pole of said source to be gripped or otherwise contacted by the subject in use characterised in that said tip (22) of the first electrode is conical in shape terminating at an acute point having an included angle of taper within the range of from 45 to 60 degs.

2. A device as in claim 1 characterised in that said angle is around 50 deg.

3. A device as in claim 1 characterised in that the first electrode has a diameter of not more than 5 mm at its merging with the greatest diameter end of the conical tip (22).

4. A device as in claim 1 characterised in that at least the tip (22) of the first electrode is formed from stainless steel or other hard corrosion-resistant metal.

5. A device as in claim 1 characterised in that the tip (22) is sheathed in an insulating material (18) leaving only said point thereof exposed.

6. A device as in claim 1 characterised in that the second electrode (26) is constituted by a portion of the housing (10), the housing being shaped to be gripped in the subject's hand for electrical contact therewith.

7. A device as in claim 6 characterised in that said portion (26) of the housing is rendered electrically conductive by being moulded or otherwise formed from a plastics compound which includes a metal powder.

8. A device as in claim 1 characterised in that it includes an indicator light or other indicator device (24) to show when current is flowing through the electrode circuit.

9. A device as in claim 1 characterised in that the D.C. power source operatively includes a 9 volt battery (21) and a resistor (23) in series with the electrodes (16,26) whereby the current operatively applied through the first electrode tip (22) is less than 2 ma.

10. A device as in claim 9 characterised in that said current is around 0.7 to 0.9 ma.

11. A device as in claim 1 characterised in that the housing (10) includes or carries a magnifying or other mirror (14).

12. A device as in claim 11 characterised in that the mirror (14) is carried on a hinged flap (12) which overlies a remaining part of the housing (10) when not in use and protects the tip (22) of the first electrode when the probe (16) is stowed in a location provided on the housing.

13. A device as in claim 1 characterised in that the housing (10) incorporates an illuminating light source powered electrically from a battery carried in the housing.

* * * * *